United States Patent
Edelbrock et al.

(10) Patent No.: US 8,617,367 B2
(45) Date of Patent: Dec. 31, 2013

(54) ELECTROCHEMICAL TEST SENSOR WITH REDUCED SAMPLE VOLUME

(75) Inventors: Andrew J. Edelbrock, Granger, IN (US); Steven C. Charlton, Osceola, IN (US)

(73) Assignee: Bayer Healthcare LLC, Whippany, NJ (US)

( * ) Notice: Subject to any disclaimer, the term of this patent is extended or adjusted under 35 U.S.C. 154(b) by 422 days.

(21) Appl. No.: 12/226,796

(22) PCT Filed: May 3, 2007

(86) PCT No.: PCT/US2007/010614
§ 371 (c)(1),
(2), (4) Date: Oct. 28, 2008

(87) PCT Pub. No.: WO2007/133457
PCT Pub. Date: Nov. 22, 2007

(65) Prior Publication Data
US 2009/0071847 A1    Mar. 19, 2009

Related U.S. Application Data

(60) Provisional application No. 60/798,797, filed on May 8, 2006.

(51) Int. Cl.
*G01N 33/487*    (2006.01)
(52) U.S. Cl.
USPC ............ 204/403.01; 204/403.02; 204/403.03; 204/403.04; 204/403.05; 205/777.5; 205/792
(58) Field of Classification Search
USPC .............. 204/403.01–403.15; 205/777.5, 792
See application file for complete search history.

(56) References Cited

U.S. PATENT DOCUMENTS

| 5,512,159 A | 4/1996 | Yoshioka et al. ............. 204/403 |
| 5,628,890 A | 5/1997 | Carter et al. .................. 204/403 |

(Continued)

FOREIGN PATENT DOCUMENTS

| EP | 1 447 452 | 8/2004 | |
| EP | 1 635 170 A1 | 3/2006 | .......... G01N 27/327 |

(Continued)

OTHER PUBLICATIONS

Written Opinion corresponding to International Patent Application No. PCT/US2007/010614, European Patent Office, dated Sep. 3, 2008, 10 pages.

(Continued)

*Primary Examiner* — Bach Dinh
(74) *Attorney, Agent, or Firm* — Nixon Peabody LLP (57) ABSTRACT

An electrochemical test sensor for detecting the analyte concentration of a fluid test sample includes a base, a dielectric layer, a reagent layer and a lid. The base provides a flow path for the test sample having on its surface a counter electrode and a working electrode adapted to electrically communicate with a detector of electrical current. The dielectric layer forms a dielectric window therethrough. The reagent layer includes an enzyme that is adapted to react with the analyte. The lid is adapted to mate with the base and to assist in forming a capillary space with an opening for the introduction of the test sample thereto. At least a portion of the width of the counter electrode is greater than the width of the working electrode.

14 Claims, 7 Drawing Sheets

(56) References Cited

U.S. PATENT DOCUMENTS

| | | | |
|---|---|---|---|
| 6,531,040 B2 | 3/2003 | Musho et al. | 204/401 |
| 6,616,819 B1 | 9/2003 | Liamos et al. | 204/403.02 |
| 6,841,052 B2 | 1/2005 | Musho et al. | 204/401 |
| 7,276,146 B2 | 10/2007 | Wilsey | |
| 2001/0006149 A1* | 7/2001 | Taniike et al. | 204/403 |
| 2002/0053523 A1* | 5/2002 | Liamos et al. | 205/787 |
| 2003/0132110 A1* | 7/2003 | Hasegawa et al. | 204/403.02 |
| 2004/0079653 A1* | 4/2004 | Karinka et al. | 205/792 |
| 2004/0096928 A1* | 5/2004 | Hasegawa et al. | 435/25 |
| 2004/0222092 A1 | 11/2004 | Musho et al. | |
| 2004/0251131 A1* | 12/2004 | Ueno et al. | 204/403.01 |
| 2004/0251132 A1* | 12/2004 | Leach et al. | 204/403.01 |
| 2005/0023136 A1 | 2/2005 | Leach et al. | 204/403.01 |
| 2005/0098432 A1* | 5/2005 | Gundel | 204/403.02 |
| 2006/0042943 A1* | 3/2006 | Shiraki et al. | 204/403.1 |
| 2006/0131171 A1* | 6/2006 | Kobayashi | 204/403.01 |

FOREIGN PATENT DOCUMENTS

| | | | |
|---|---|---|---|
| JP | 2000-221157 | 8/2000 | G01N 27/327 |
| JP | 2004-154547 | 6/2004 | A61B 5/00 |
| JP | 2004-33125 | 9/2004 | |
| JP | 2004-245836 | 9/2004 | C12Q 1/00 |
| JP | WO2004/113903 * | 12/2004 | |
| JP | 2005-512027 | 4/2005 | |
| KR | WO03097866 A1 * | 11/2003 | |
| WO | WO 92/19959 | 11/1992 | G01N 33/543 |
| WO | WO 2004/113901 A1 | 12/2004 | G01N 27/30 |
| WO | WO 2005/078436 A1 | 8/2005 | G01N 33/487 |
| WO | WO2005/078436 A1 * | 8/2005 | |

OTHER PUBLICATIONS

International Search Report corresponding to International Patent Application No. PCT/US2007/010614, European Patent Office, dated Sep. 3, 2008, 4 pages.

* cited by examiner

ELECTROCHEMICAL TEST SENSOR WITH REDUCED SAMPLE VOLUME

CROSS-REFERENCE TO RELATED APPLICATIONS

This application claims priority to Application No. 60/798,797 filed on May 8, 2006, which is incorporated by reference in its entirety.

FIELD OF THE INVENTION

The present invention relates generally to electrochemical test sensors, and more specifically to a test sensor that is adapted to determine the concentration of an analyte.

BACKGROUND OF THE INVENTION

Medical conditions such as diabetes require a person afflicted with the condition to regularly self-monitor that person's blood-glucose concentration level. The purpose of monitoring the blood glucose concentration level is to determine the person's blood glucose concentration level and then to take corrective action, based upon whether the level is too high or too low, to bring the level back within a normal range. The failure to take corrective action may have serious medical implications for that person.

One method of monitoring a person's blood glucose level is with a portable testing device. The portable nature of these devices enables users to conveniently test their blood glucose levels at different locations. One type of device utilizes an electrochemical test sensor to harvest and analyze the blood sample. The test sensor typically includes a capillary channel to receive the blood sample and a plurality of electrodes. Some electrochemical test sensor devices have larger capillary channels than are optimally desired. The bigger the capillary channel, the more blood from a person is required to fill the channel. Because drawing blood from a person is unpleasant, it would also be desirable to reduce the size of the capillary channel to require less blood. However, there must be sufficient blood to cover and activate the plurality of electrodes used in the electrochemical test sensor. Thus, there exists a need for an electrochemical test sensor with a smaller capillary channel without sacrificing the accuracy of the analyte concentration determination.

SUMMARY OF THE INVENTION

According to one embodiment, an electrochemical test sensor for detecting the concentration of an analyte in a fluid test sample comprises a base, dielectric layer, a reagent layer and a lid. The base provides a flow path for the fluid test sample having on its surface a counter electrode and a working electrode adapted to electrically communicate with a detector of electrical current. The dielectric layer forms a dielectric window therethrough. The reagent layer includes an enzyme that is adapted to react with the analyte. The lid is adapted to mate with the base and to assist in forming a capillary space with an opening for the introduction of the fluid test sample thereto. The dielectric layer and the reagent layer are located between the base and the lid. The working electrode is defined in one dimension by the dielectric window. The counter electrode is defined in one dimension by the dielectric window and the capillary space.

According to one embodiment, an electrochemical test sensor for detecting the concentration of an analyte in a fluid test sample comprises a base, dielectric layer, a reagent layer and a lid. The base provides a flow path for the fluid test sample having on its surface a counter electrode and a working electrode adapted to electrically communicate with a detector of electrical current. The dielectric layer forms a dielectric window therethrough. The reagent layer includes an enzyme that is adapted to react with the analyte. The lid is adapted to mate with the base and to assist in forming a capillary space with an opening for the introduction of the fluid test sample thereto. The dielectric layer and the reagent layer are located between the base and the lid. At least a portion of the width of the counter electrode is greater than the width of the working electrode.

According to one method, an analyte concentration in a fluid sample is determined with a test sensor. An electrochemical test sensor is provided that includes a base, a dielectric layer, a reagent layer and a lid. The base provides a flow path for the fluid test sample having on its surface a counter electrode and a working electrode adapted to electrically communicate with a detector of electrical current. The dielectric layer forms a dielectric window therethrough. The reagent layer includes an enzyme that is adapted to react with the analyte. The lid is adapted to mate with the base and to assist in forming a capillary space with an opening for the introduction of the fluid test sample thereto. The dielectric layer and the reagent layer are located between the base and the lid. At least a portion of the width of the counter electrode is greater than the width of the working electrode. The reagent layer contacts the fluid sample via the capillary space. An electrical signal is generated in the test sensor in response to the presence of the analyte. A level of the analyte is determined from the electrical signal.

According to a further embodiment, an electrochemical test sensor for detecting the concentration of an analyte in a fluid test sample comprises a base, a spacer layer, a reagent layer and a lid. The base that provides a flow path for the fluid test sample having on its surface a counter electrode and a working electrode adapted to electrically communicate with a detector of electrical current. The spacer layer forms a spacer window therethrough. The reagent layer includes an enzyme that is adapted to react with the analyte. The lid is adapted to mate with the base and the spacer layer to assist in forming a capillary space with an opening for the introduction of the fluid test sample thereto. The dielectric layer and the reagent layer are located between the base and the lid. The working electrode is defined in one dimension by the dielectric window. The counter electrode is defined in one dimension by the dielectric window and the capillary space.

According to yet another embodiment, an electrochemical test sensor for detecting the concentration of an analyte in a fluid test sample comprises a base, a spacer layer, a reagent layer and a lid. The base provides a flow path for the fluid test sample having on its surface a counter electrode and a working electrode adapted to electrically communicate with a detector of electrical current. The spacer layer forms a spacer window therethrough. The reagent layer includes an enzyme that is adapted to react with the analyte. The lid is adapted to mate with the base and the spacer layer to assist in forming a capillary space with an opening for the introduction of the fluid test sample thereto. The dielectric layer and the reagent layer are located between the base and the lid. At least a portion of the width of the counter electrode is greater than the width of the working electrode.

According to another method, an analyte concentration in a fluid sample is determined with a test sensor. An electrochemical test sensor is provided and includes a base, a reagent layer, a spacer layer and a lid. The base provides a flow path for the fluid test sample having on its surface a counter electrode and a working electrode adapted to electrically communicate with a detector of electrical current. The spacer layer forms a spacer window therethrough. The reagent layer includes an enzyme that is adapted to react with the analyte. The lid is adapted to mate with the base and the spacer layer to assist in forming a capillary space with an opening for the introduction of the fluid test sample thereto. The dielectric layer and the reagent layer are located between the base and the lid. At least a portion of the width of the counter electrode is greater than the width of the working electrode. The reagent layer contacts the fluid sample via the capillary space. An electrical signal is generated in the test sensor in response to the presence of the analyte. A level of the analyte is determined from the electrical signal.

DESCRIPTION OF ILLUSTRATED EMBODIMENTS

The present invention is directed to an electrochemical test sensor meter that is adapted to be placed into a meter or an instrument and assist in determining an analyte concentration in a body fluid sample. The electrochemical sensor of the present invention assists in reducing the volume of the fluid sample needed to properly determine the analyte concentration. The body fluid sample may be collected with a lancing device.

Examples of the types of analytes that may be collected include glucose, lipid profiles (e.g., cholesterol, triglycerides, LDL and HDL), microalbumin, hemoglobin $A_{1C}$, fructose, lactate, or bilirubin. It is contemplated that other analyte concentrations may also be determined. The analytes may be in, for example, a whole blood sample, a blood serum sample, a blood plasma sample, other body fluids like ISF (interstitial fluid) and urine, and non-body fluids. As used within this application, the term "concentration" refers to an analyte concentration, activity (e.g., enzymes and electrolytes), titers (e.g., antibodies), or any other measure concentration used to measure the desired analyte.

Figure 1:
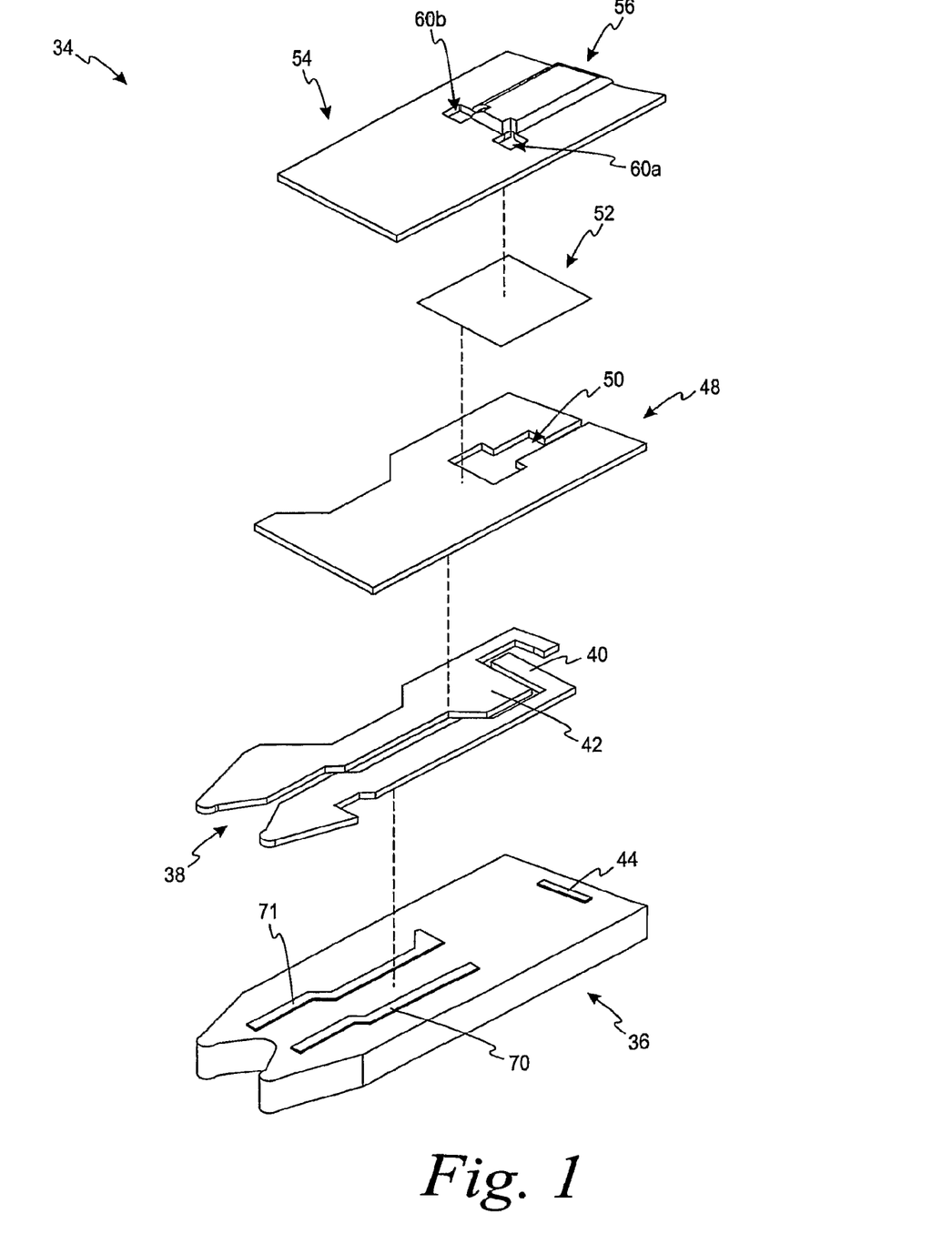
FIG. 1 is an exploded view of an electrochemical test sensor according to one embodiment.
Figure 2:
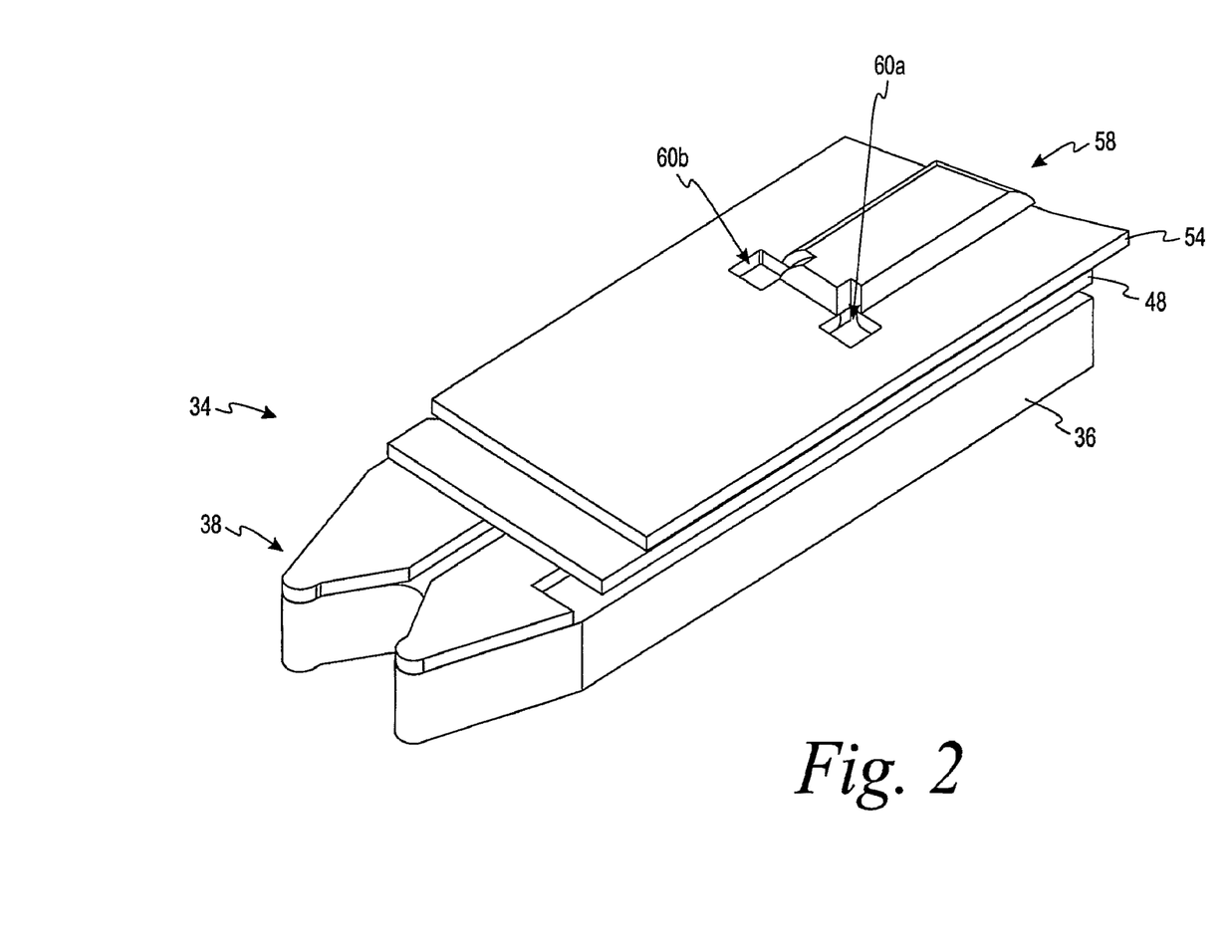
FIG. 2 is a perspective view of the assembled electrochemical test sensor of FIG. 1.
Figure 3:
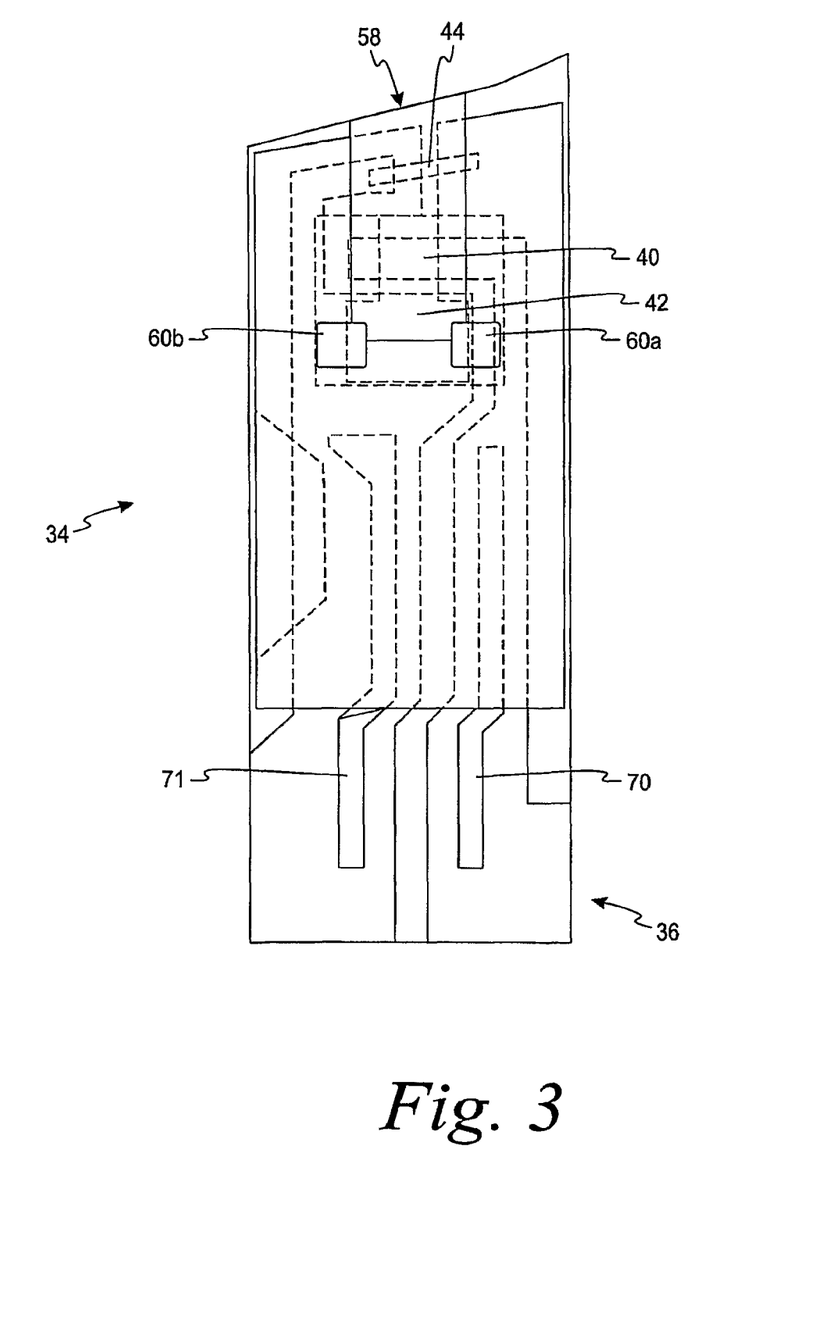
FIG. 3 is a top view of the assembled electrochemical test sensor of FIG. 1.

Referring initially to FIGS. 1-3, an electrochemical test sensor 34 includes an insulating base 36, a meter-contact area 38, a plurality of electrodes 40, 42 and 44, a dielectric layer 48, a reagent layer 52 and a lid 54. The plurality of electrodes in FIG. 3 includes a working electrode 40, a counter electrode 42 and a trigger electrode 44. The electrochemical test sensor 34 may be printed in sequence such as by a screen-printing technique. It is contemplated that the electrochemical test sensor may be formed by other methods.

The function of the reagent layer 52 of FIG. 1 is to convert an analyte (e.g., glucose) in the fluid test sample, stoichiometrically into a chemical species that is electrochemically measurable, in terms of electrical current it produces, by the components of the working electrode 40 and the counter electrode 42. The reagent layer 52 typically includes an enzyme and an electron acceptor. The enzyme reacts with the analyte to produce mobile electrons on the working and counter electrodes 40, 42. For example, the reagent layer may include glucose oxidase or glucose dehydrogenase if the analyte to be determined is glucose. The enzyme in the reagent layer 52 may be combined with a hydrophilic polymer such as poly(ethylene oxide) or other polymers such as polyethylene oxide (PEO), hydroxyethyl cellulose (HEC), carboxymethylcellulose (CMC) and polyvinyl acetate (PVA). The electron acceptor (e.g., ferricyanide salt) carries the mobile electrons to the surface of the working electrode 40.

Figure 4A:
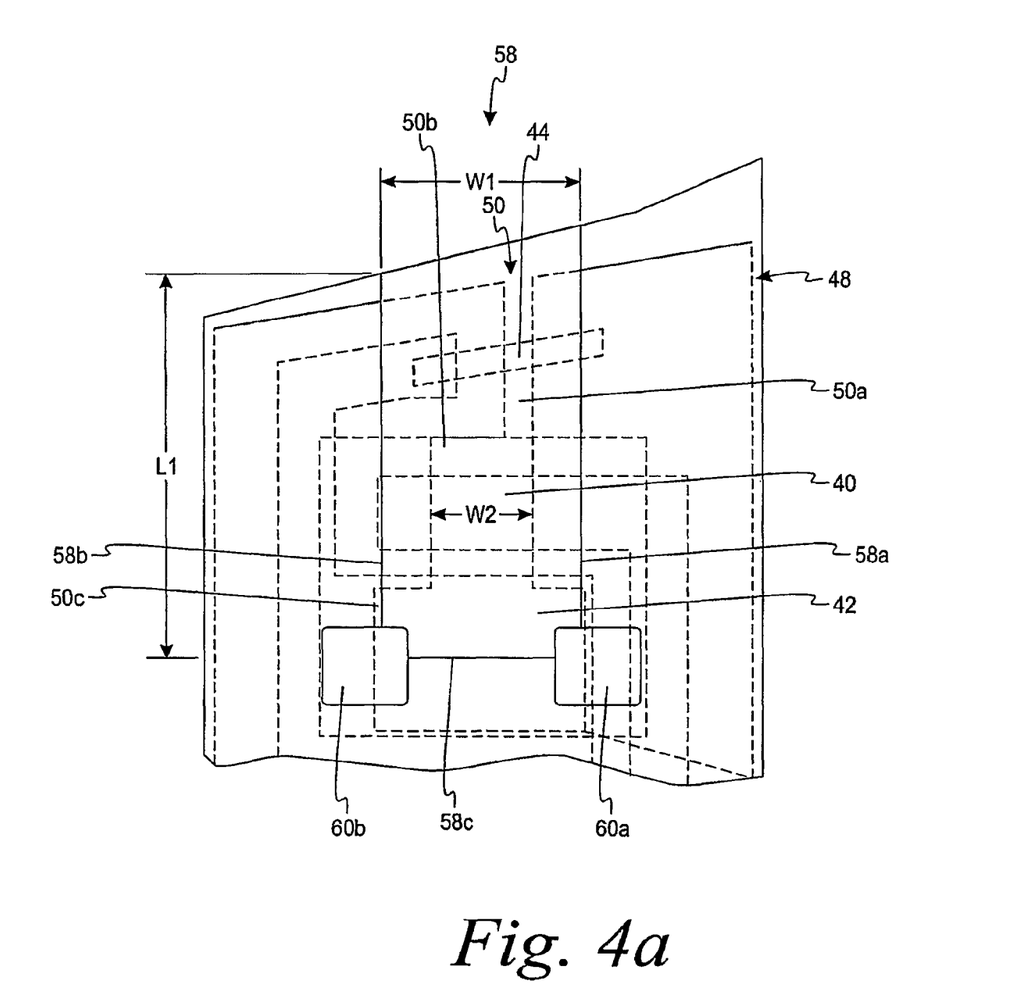
FIG. 4a is an enlarged top portion of the assembled electrochemical test sensor of FIG. 3.

The dielectric layer 48 of FIGS. 1 and 4a limits the electrical area that is ultimately formed. Specifically, the dielectric layer 48 of FIGS. 1 and 4a forms a dielectric window 50 that defines the working electrode 40 and assists in partially defining the counter electrode 42 as will be discussed below. The dielectric window 50 includes a first dielectric window section 50a, a second dielectric window section 50b and a third dielectric window section 50c. The dielectric layer may be formed by a variety of methods such as printing or die-cutting of a pressure-sensitive adhesive. It is contemplated that the dielectric layer may be formed by other methods.

The working electrode 40 and the counter electrode 42 assist in electrochemically determining the analyte concentration. In one embodiment, the working electrode 40 and the counter electrode 42 comprise a mixture of amorphous and graphite forms of carbon that is chosen to be electrochemically active and provide a low electrical resistance path between the electrodes and the meter or instrument with which they are in operative connection via the meter-contact area 38. In another embodiment, the working electrode 40 and the counter electrode 42 comprises a mixture of carbon and silver. It is contemplated that the working electrode and counter electrode may be made of other materials that assist in providing an electrical path to the meter or instrument with which they are in operative connection. It is contemplated that additional conductors may be added. For example, in FIG. 1, first and second conductors 70, 71 comprise a highly conductive carbon-silver ink that may be printed to further reduce the electrical resistance from the working and counter electrodes 40, 42 to the meter-contact area 38.

In the electrochemical sensor 34 of FIG. 1, the optional trigger electrode 44 assists in determining whether a sufficient fluid sample (e.g., blood) has been placed on the electrochemical test sensor 34. It is contemplated that an electrochemical sensor may include other electrodes such as an underfill electrode, hematocrit-detection electrode or other electrodes.

Referring still to FIG. 1, the lid 54 forms a concave space 56 over the base 36 and the components located thereon eventually form a capillary space or channel (see capillary space or channel 58 of FIGS. 2 and 4a). The lid 54 may be formed by embossing a flat sheet of deformable material and then joining the lid 54 and the base 36 in a sealing operation. The material forming the lid 54 may be a deformable polymeric sheet material (e.g., polycarbonate or an embossable grade of polyethylene terephthalate), or a glycol modified polyethylene terephthalate. It is contemplated that other materials may be used in forming the lid.

The material forming the lid 54 may be punctured to provide at least one air vent 60*a,b*. The air vents 60*a,b* are desirably because they assist in preventing or inhibiting air-lock. By preventing or inhibiting air-lock, a fluid sample is better able to enter the capillary channel 58 in a timely manner.

As shown in FIG. 4*a*, the width W1 of the capillary channel 58 at the location of the working electrode 40 is wider than the width W2 of the second dielectric window section 50*b*. The width W1 should be of a sufficient width to ensure that the second dielectric window section 50*b* remains entirely within the capillary channel 58 under normal manufacturing assembly tolerances. For example, in FIG. 4*a*, the width W1 of the capillary channel 58 is about twice the width W2 of the second dielectric window section 50*b*. The width of the capillary channel is generally from about 1.2 to about 5 times the width of the dielectric window section that assists in forming the working electrode. By having the second dielectric window section 50*b* remain entirely within the capillary channel 58, the defined area of the working electrode 40 remains constant. It is important for the area of the working electrode to remain substantially the same so as to obtain an accurate reading of the analyte.

Suitable materials for the insulating base 36 of FIG. 1 include polymeric materials, such as polycarbonate, polyethylene terephthalate, dimensionally stable vinyl and acrylic polymers, and blends thereof. The insulating base may be formed from metal foil structures such as a nylon/aluminum/polyvinyl chloride laminate. It is contemplated that other materials may be used in forming the insulating base.

The lid 54 and the base 36 may be sealed together by a variety of methods. For example, the lid 54 and the base 36 may be sealed together by sonic welding in which the base 36 and the lid 54 are first aligned and then pressed together between a vibratory heat sealing member or horn and a stationary jaw. In this method, the horn is shaped such that contact is made only with the flat, non-embossed regions of the lid 54. Ultrasonic energy from a crystal or other transducer is used to excite vibrations in the metal horn. This mechanical energy is dissipated as heat in the polymeric joint allowing the bonding of the thermoplastic materials. In another method, the lid 54 and the base 36 are joined by using an adhesive material on the underside of the lid 54. It is contemplated that other methods may be used to attached the lid and the base.

Referring back to FIG. 4*a*, the working electrode 40 and the counter electrode 42 are shown in more detail. The counter electrode 42 can vary in size with respect to the working electrode 40 to absorb any process variations that occur. In other words, the area of the counter electrode 42 is not fixed relative to the working electrode 40 but is allowed to vary over an allowable range. The counter electrode 42, however, is required to maintain a minimum size with respect to the working electrode 40. Specifically, to function properly, the area of the counter electrode 42 must be above some minimum area with respect to the area of the working electrode. For example, the area of the counter electrode is typically at least about 5 to about 10% of the area of the working electrode. The area of the counter electrode is generally from about 25% to about 350% of the area of the working electrode. For example, if the area of the working electrode is fixed at 0.65 mm$^2$, then the area of the counter electrode is generally from about 0.13 mm$^2$ to about 2.5 mm$^2$.

A portion of the counter electrode 42 of FIG. 4*a* spans the entire width of the capillary channel 58. By having at least a portion of the entire width of the counter electrode 42 span the capillary channel 58, the capillary channel 58 can be made smaller while still having a desirable area of the counter electrode. By reducing the size of the capillary channel 58, a lower volume of test fluid is needed. In this embodiment, the capillary channel is less than about 1 µL. It is contemplated that the capillary channel may even be smaller such as less than about 0.85 µL or even less than about 0.75 µL.

Figure 4B:
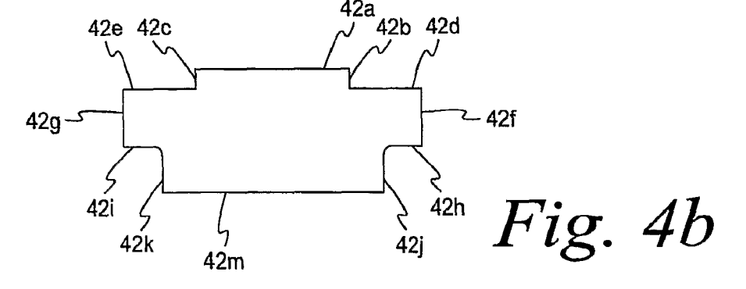
FIG. 4b is an enlarged top view of the counter electrode in the assembled electrochemical test sensor of FIG. 3.

Referring to FIG. 4*b*, the counter electrode 42 has been enlarged to show the components that assist in forming the counter electrode 42. Specifically, outer portions 42*a*-42*m* form the outer periphery of the counter electrode 42. Section 42*a* is formed by the initial placement of the electrical ink onto the base 36. Section 42*b*, 42*c*, 42*d*, 42*e* are formed by the third dielectric window section 50*c*. Sections 42*f*, 42*g* are formed by sides 58*a*, 58*b* (see FIG. 4*a*) of the capillary channel 58. Sections 42*h*, 42*i*, 42*j* and 42*k* are formed by the air vents 60*a, b*. Section 42*m* is formed from an end 58*c* (see FIG. 4*a*) of the capillary channel 58. Thus, in this embodiment, the counter electrode is formed by placement of the ink in one dimension, and the dielectric window section, the capillary channel and the air vents assist in defining the counter electrode in another dimension. The shape of the counter electrode 42 of FIG. 4*b* is in the shape of a general "T".

Figure 4C:
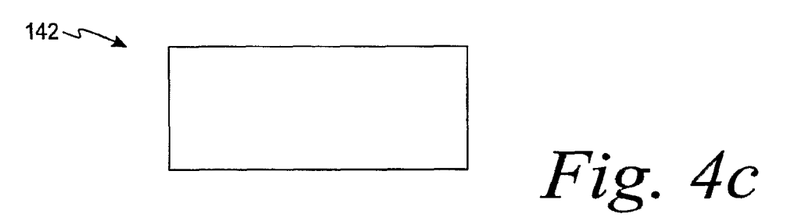
FIG. 4c is an enlarged top view of a counter electrode according to another embodiment.
Figure 4D:
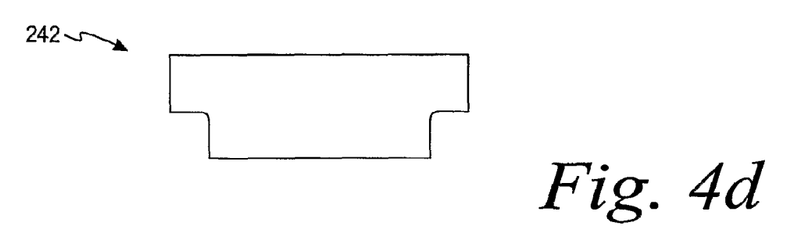
FIG. 4d is an enlarged top view of a counter electrode according to a further embodiment.
Figure 4E:
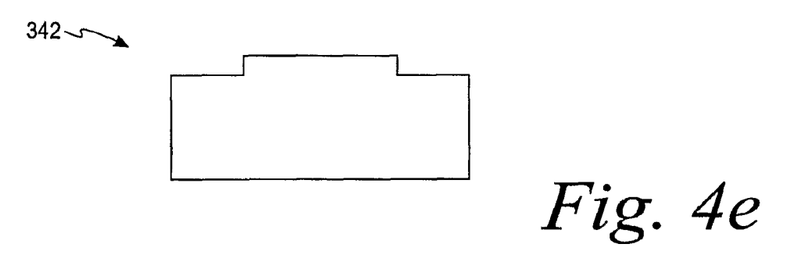
FIG. 4e is an enlarged top view of a counter electrode according to yet another embodiment.
Figure 4F:
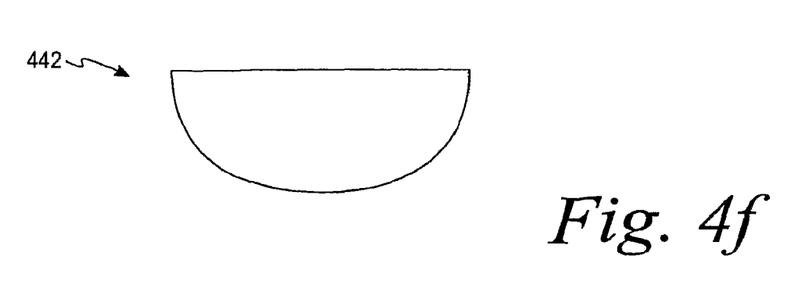
FIG. 4f is an enlarged top view of a counter electrode according to another embodiment.

It is contemplated that the counter electrode may be formed by less components. Turning to FIG. 4*c*, a counter electrode 142 according to another embodiment is a generally rectangular shape. The counter electrode 142 is formed by placement of the ink in one dimension and the second dimension is formed by a dielectric window section and a capillary channel. Referring to FIG. 4*d*, a counter electrode 242 according to another embodiment is shown. The counter electrode 242 is formed by placement of the ink in one dimension and the second dimension is formed by a dielectric window section, a capillary channel, and a plurality of air vents. Referring to FIG. 4*e*, a counter electrode 342 according to a further embodiment is shown. The counter electrode 342 is formed by placement of the ink in one dimension and the second dimension is formed by a dielectric window section and a capillary channel. Another counter electrode embodiment is depicted in FIG. 4*f* with counter electrode 442. It is contemplated that the shape of the counter electrode may be shapes other than depicted in the figures, including polygonal and non-polygonal shapes. It is desirable, however, for the shape of the counter electrode to be of a shape that substantially fills the capillary channel so as to result in the reduction of the capillary channel size.

Figure 5:
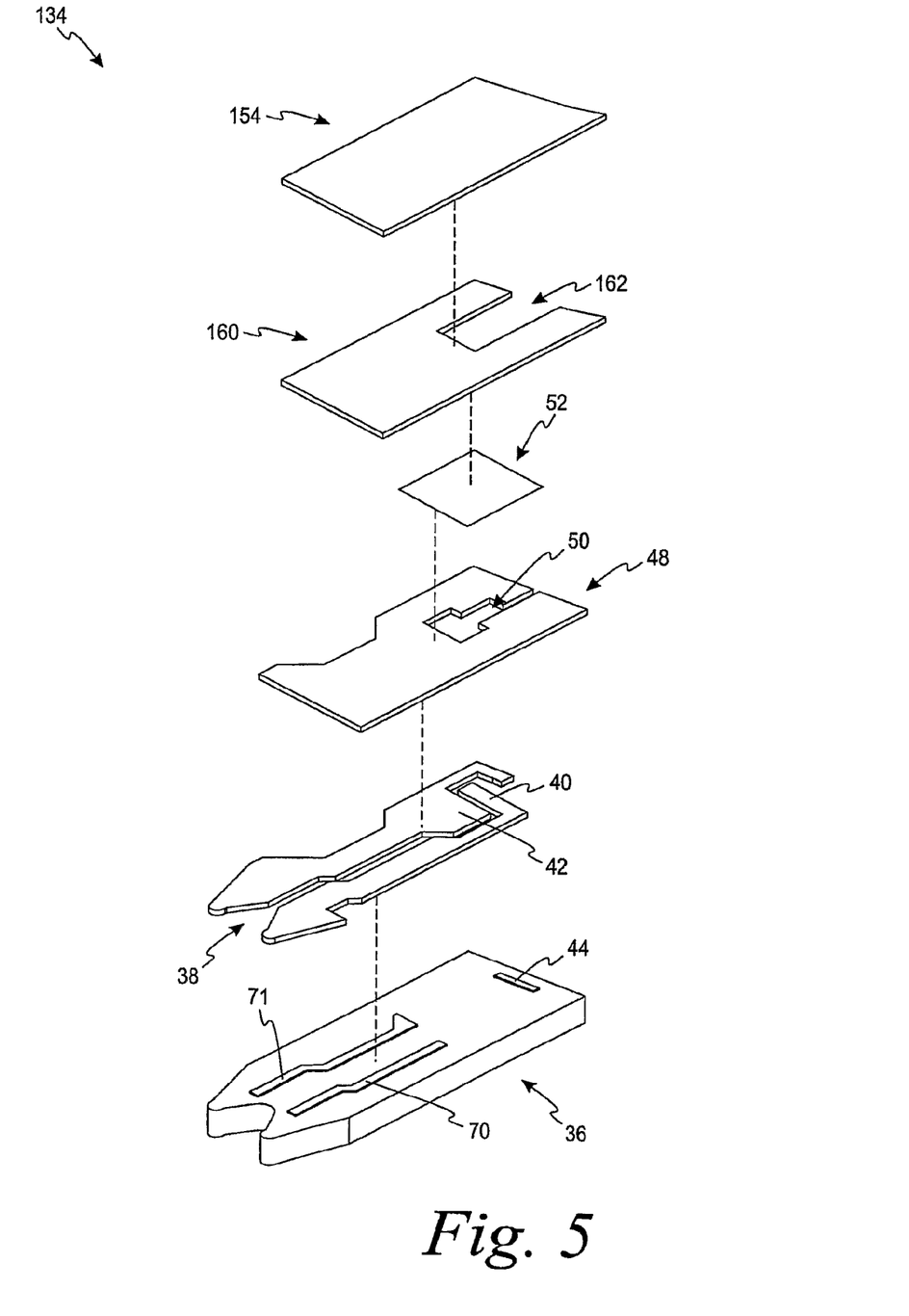
FIG. 5 is an exploded view of an electrochemical test sensor including a spacer according to one embodiment.

The design of the working electrode of the present invention is not limited to use with a three-dimensional embossed lid forming a concave space, such as the lid 54. Other ways of forming a concave space over a working electrode in an electrochemical test sensor may also be used in accordance with the present invention. For example, FIG. 5 depicts an electrochemical test sensor 134 according to another embodiment. The electrochemical test sensor 134 includes the base 36, a meter-contact area 38, the working electrode 40, the counter electrode 42, and the reagent layer 52. The electrochemical test sensor 134 further includes a lid 154 and a spacer 160. The spacer 160 includes a spacer opening 162 formed therein. The spacer opening 162 assists in forming the capillary channel or space when the lid 154 is mated with the spacer 160 and the base 36. The electrochemical test sensor 134 functions in much the same way as electrochemical test sensor 34 with the main difference being the method of forming the spacer opening 162 as compared to the concave space 48.

Figure 6:
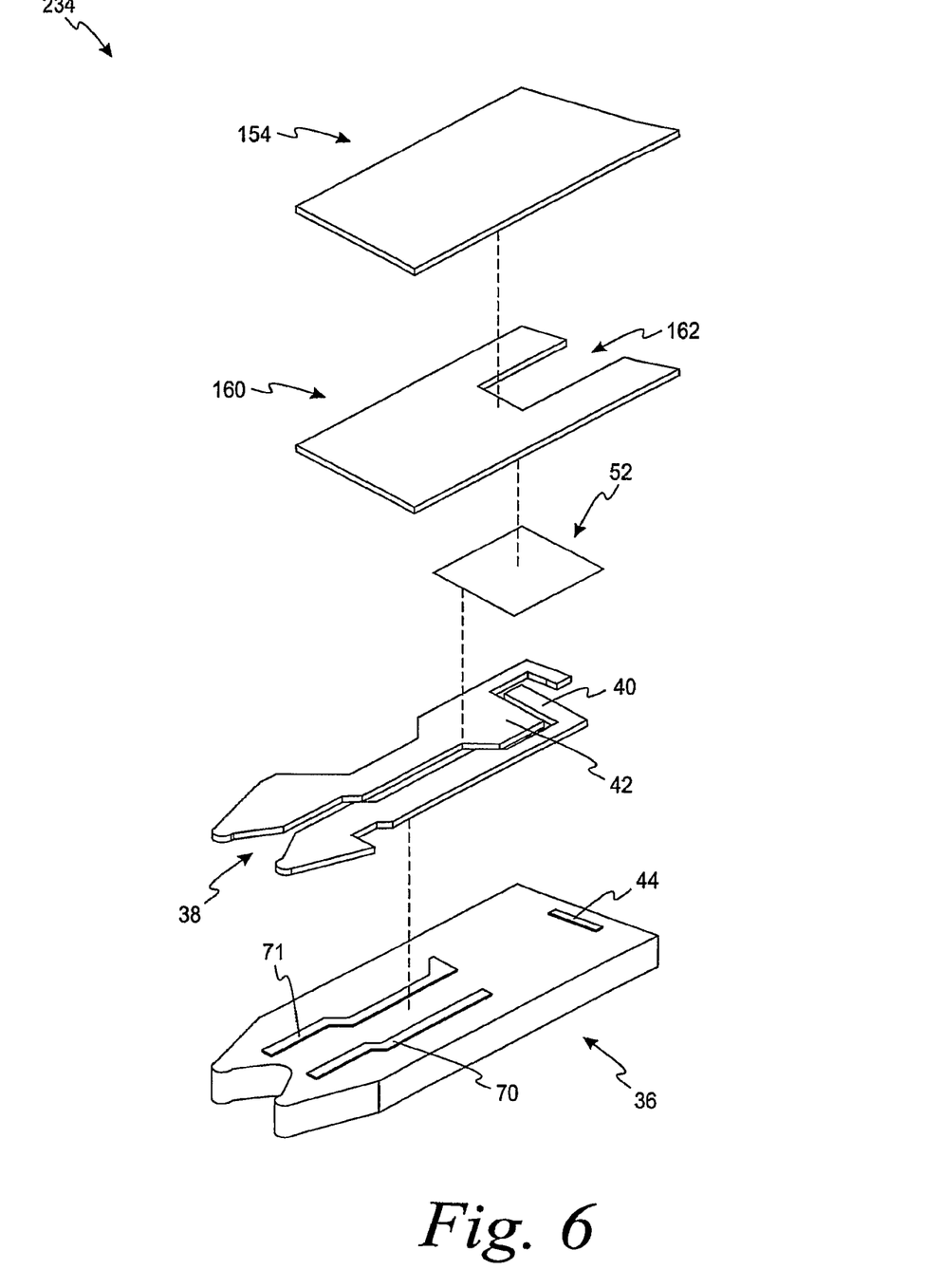
FIG. 6 is an exploded view of an electrochemical test sensor including a spacer according to another embodiment.

Referring to FIG. 6, another electrochemical test sensor (electrochemical test sensor 234) is depicted. The electrochemical test sensor 234 functions in a similar manner as discussed above in connection with electrochemical test sensors 34, 134. The electrochemical test sensor 234 is the same as the electrochemical test sensor 134 except that the electrochemical test sensor 234 does not include a dielectric layer.

Embodiment A

An electrochemical test sensor for detecting the concentration of an analyte in a fluid test sample, the electrochemical test sensor comprising:
a base that provides a flow path for the fluid test sample having on its surface a counter electrode and a working electrode adapted to electrically communicate with a detector of electrical current;
a dielectric layer forming a dielectric window therethrough;
a reagent layer including an enzyme that is adapted to react with the analyte; and
a lid adapted to mate with the base and to assist in forming a capillary space with an opening for the introduction of the fluid test sample thereto,
wherein the dielectric layer and the reagent layer are located between the base and the lid,
wherein the working electrode is defined in one dimension by the dielectric window,
wherein the counter electrode is defined in one dimension by the dielectric window and the capillary space.

Embodiment B

The electrochemical test sensor of embodiment A wherein the lid further forms at least one air vent, the counter electrode being further defined by the at least one air vent in the one dimension.

Embodiment C

The electrochemical test sensor of embodiment A wherein the counter electrode extends across the full width of the capillary space.

Embodiment D

The electrochemical test sensor of embodiment A wherein the reagent layer includes glucose oxidase.

Embodiment E

The electrochemical test sensor of embodiment A wherein the reagent layer includes glucose dehydrogenase.

Embodiment F

The electrochemical test sensor of embodiment A wherein the counter electrode is generally T-shaped.

Embodiment G

The electrochemical test sensor of embodiment A wherein the counter electrode is a polygonal shape.

Embodiment H

The electrochemical test sensor of embodiment A wherein the counter electrode is a non-polygonal shape.

Embodiment I

The electrochemical test sensor of embodiment A wherein the volume of the capillary space is less than about 1 µL.

Embodiment J

The electrochemical test sensor of embodiment A further including a spacer, the spacer being located between the lid and the reagent layer.

Embodiment K

An electrochemical test sensor for detecting the concentration of an analyte in a fluid test sample, the electrochemical test sensor comprising:
a base that provides a flow path for the fluid test sample having on its surface a counter electrode and a working electrode adapted to electrically communicate with a detector of electrical current;
a dielectric layer forming a dielectric window therethrough;
a reagent layer including an enzyme that is adapted to react with the analyte; and
a lid adapted to mate with the base and to assist in forming a capillary space with an opening for the introduction of the fluid test sample thereto,
wherein the dielectric layer and the reagent layer are located between the base and the lid,
wherein at least a portion of the width of the counter electrode is greater than the width of the working electrode.

Embodiment L

The electrochemical test sensor of embodiment K wherein the counter electrode is defined in one dimension by the dielectric window and the capillary space.

Embodiment M

The electrochemical test sensor of embodiment L wherein the counter electrode is defined in the one dimension by an end and sides of the capillary space.

Embodiment N

The electrochemical test sensor of embodiment K wherein the lid further forms at least one air vent.

Embodiment O

The electrochemical test sensor of embodiment K wherein the counter electrode extends across the full width of the capillary space.

Embodiment P

The electrochemical test sensor of embodiment K wherein the reagent layer includes glucose oxidase.

Embodiment Q

The electrochemical test sensor of embodiment K wherein the reagent layer includes glucose dehydrogenase.

Embodiment R

The electrochemical test sensor of embodiment K wherein the counter electrode is generally T-shaped.

Embodiment S

The electrochemical test sensor of embodiment K wherein the counter electrode is a polygonal shape.

Embodiment T

The electrochemical test sensor of embodiment K wherein the counter electrode is a non-polygonal shape.

Embodiment U

The electrochemical test sensor of embodiment K wherein the volume of the capillary space is less than about 1 µL.

Embodiment V

The electrochemical test sensor of embodiment K further including a spacer, the spacer being located between the lid and the reagent layer.

Process W

A method for determining the concentration of an analyte in a fluid sample with a test sensor, the method comprising the acts of:
providing an electrochemical test sensor including a base, a dielectric layer, a reagent layer and a lid, the base providing a flow path for the fluid test sample having on its surface a counter electrode and a working electrode adapted to electrically communicate with a detector of electrical current, the dielectric layer forming a dielectric window therethrough, the reagent layer including an enzyme that is adapted to react with the analyte, the lid being adapted to mate with the base and to assist in forming a capillary space with an opening for the introduction of the fluid test sample thereto, the dielectric layer and the reagent layer being located between the base and the lid and at least a portion of the width of the counter electrode being greater than the width of the working electrode;
contacting the reagent layer with the fluid sample via the capillary space;
generating an electrical signal in the test sensor in response to the presence of the analyte; and
determining a level of the analyte from the electrical signal.

Process X

The method of process W wherein the electrochemical test sensor is formed by a screen-printing technique.

Process Y

The method of process W wherein the analyte is glucose.

Process Z

The method of process W wherein the working electrode is defined in one dimension by the dielectric window and wherein the counter electrode is defined in one dimension by the dielectric window and the capillary space.

Process AA

The method of process W wherein the lid further forms at least one air vent.

Process BB

The method of process W wherein the counter electrode extends across the full width of the capillary space.

Process CC

The method of process W wherein the counter electrode is generally T-shaped.

Process DD

The method of process W wherein the counter electrode is a polygonal shape.

Process EE

The method of process W wherein the counter electrode is a non-polygonal shape.

Process FF

The method of process W wherein the volume of the capillary space is less than about 1 µL.

Process GG

The method of process W wherein the electrochemical test sensor further includes a spacer, the spacer being located between the lid and the reagent layer.

Embodiment HH

An electrochemical test sensor for detecting the concentration of an analyte in a fluid test sample, the electrochemical test sensor comprising:
a base that provides a flow path for the fluid test sample having on its surface a counter electrode and a working electrode adapted to electrically communicate with a detector of electrical current;
a spacer layer forming a spacer window therethrough;
a reagent layer including an enzyme that is adapted to react with the analyte; and
a lid adapted to mate with the base and the spacer layer to assist in forming a capillary space with an opening for the introduction of the fluid test sample thereto,
wherein the dielectric layer and the reagent layer are located between the base and the lid,
wherein the working electrode is defined in one dimension by the dielectric window,
wherein the counter electrode is defined in one dimension by the dielectric window and the capillary space.

Embodiment II

The electrochemical test sensor of embodiment HH wherein the lid further forms at least one air vent, the counter electrode being further defined by the at least one air vent in the one dimension.

Embodiment JJ

The electrochemical test sensor of embodiment HH wherein the counter electrode extends across the full width of the capillary space.

Embodiment KK

The electrochemical test sensor of embodiment HH wherein the reagent layer includes glucose oxidase.

Embodiment LL

The electrochemical test sensor of embodiment HH wherein the reagent layer includes glucose dehydrogenase.

Embodiment MM

The electrochemical test sensor of embodiment HH wherein the counter electrode is generally T-shaped.

Embodiment NN

The electrochemical test sensor of embodiment HH wherein the counter electrode is a polygonal shape.

Embodiment OO

The electrochemical test sensor of embodiment HH wherein the counter electrode is a non-polygonal shape.

Embodiment PP

The electrochemical test sensor of embodiment HH wherein the volume of the capillary space is less than about 1 µL.

Embodiment QQ

The electrochemical test sensor of embodiment HH further including a spacer, the spacer being located between the lid and the reagent layer.

Embodiment RR

An electrochemical test sensor for detecting the concentration of an analyte in a fluid test sample, the electrochemical test sensor comprising:
a base that provides a flow path for the fluid test sample having on its surface a counter electrode and a working electrode adapted to electrically communicate with a detector of electrical current;
a spacer layer forming a spacer window therethrough;
a reagent layer including an enzyme that is adapted to react with the analyte; and
a lid adapted to mate with the base and the spacer layer to assist in forming a capillary space with an opening for the introduction of the fluid test sample thereto,
wherein the dielectric layer and the reagent layer are located between the base and the lid,
wherein at least a portion of the width of the counter electrode is greater than the width of the working electrode.

Embodiment SS

The electrochemical test sensor of embodiment RR wherein the counter electrode is defined in one dimension by the dielectric window and the capillary space.

Embodiment TT

The electrochemical test sensor of embodiment RR wherein the counter electrode is defined in the one dimension by an end and sides of the capillary space.

Embodiment UU

The electrochemical test sensor of embodiment RR wherein the lid further forms at least one air vent, the counter electrode being further defined by the at least one air vent in the one dimension.

Embodiment VV

The electrochemical test sensor of embodiment RR wherein the counter electrode extends across the full width of the capillary space.

Embodiment WW

The electrochemical test sensor of embodiment RR wherein the reagent layer includes glucose oxidase.

Embodiment XX

The electrochemical test sensor of embodiment RR wherein the reagent layer includes glucose dehydrogenase.

Embodiment YY

The electrochemical test sensor of embodiment RR wherein the counter electrode is generally T-shaped.

Embodiment ZZ

The electrochemical test sensor of embodiment RR wherein the counter electrode is a polygonal shape.

Embodiment AAA

The electrochemical test sensor of embodiment RR wherein the counter electrode is a non-polygonal shape.

Embodiment BBB

The electrochemical test sensor of embodiment RR wherein the volume of the capillary space is less than about 1 µL.

Embodiment CCC

The electrochemical test sensor of embodiment RR further including a spacer, the spacer being located between the lid and the reagent layer.

Process DDD

A method for determining the concentration of an analyte in a fluid sample with a test sensor, the method comprising the acts of:

providing an electrochemical test sensor including a base, a reagent layer, a spacer layer and a lid, the base providing a flow path for the fluid test sample having on its surface a counter electrode and a working electrode adapted to electrically communicate with a detector of electrical current, the spacer layer forming a spacer window therethrough, the reagent layer including an enzyme that is adapted to react with the analyte, the lid being adapted to mate with the base and the spacer layer to assist in forming a capillary space with an opening for the introduction of the fluid test sample thereto, the dielectric layer and the reagent layer being located between the base and the lid and at least a portion of the width of the counter electrode being greater than the width of the working electrode;

contacting the reagent layer with the fluid sample via the capillary space;

generating an electrical signal in the test sensor in response to the presence of the analyte; and determining a level of the analyte from the electrical signal.

Process EEE

The method of process DDD wherein the electrochemical test sensor is formed by a screen-printing technique.

Process FFF

The method of process DDD wherein the analyte is glucose.

Process GGG

The method of process DDD wherein the working electrode is defined in one dimension by the dielectric window and wherein the counter electrode is defined in one dimension by the dielectric window and the capillary space.

Process HHH

The method of process DDD wherein the lid further forms at least one air vent.

Process III

The method of process DDD wherein the counter electrode extends across the full width of the capillary space.

Process JJJ

The method of process DDD wherein the counter electrode is generally T-shaped.

Process KKK

The method of process DDD wherein the counter electrode is a polygonal shape.

Process LLL

The method of process DDD wherein the counter electrode is a non-polygonal shape.

Process MMM

The method of process DDD wherein the volume of the capillary space is less than about 1 μL.

Process NNN

The method of process DDD wherein the electrochemical test sensor further includes a spacer, the spacer being located between the lid and the reagent layer.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. An electrochemical test sensor for detecting the concentration of an analyte in a fluid test sample, the electrochemical test sensor comprising:
   a base that provides a flow path for the fluid test sample having on its surface a counter electrode and a working electrode adapted to electrically communicate with a detector of electrical current;
   a dielectric layer forming a dielectric window therethrough;
   a reagent layer including an enzyme that is adapted to react with the analyte; and
   a lid adapted to mate with the base and to assist in forming a capillary space with an opening for the introduction of the fluid test sample thereto,
   wherein the dielectric layer and the reagent layer are located between the base and the lid,
   wherein an exposed portion of the working electrode for being exposed to the fluid test sample is defined in a width-wise dimension by the dielectric window,
   wherein an exposed portion of the counter electrode for being exposed to the test fluid sample is defined in a width-wise dimension by at least a portion of the dielectric window and at least a portion of the capillary space, the at least a portion of the dielectric window being different from the at least a portion of the capillary space,
   wherein a width of the exposed portion of the counter electrode defined by the dielectric window is different than a width of the exposed portion of the counter electrode defined by the capillary space.

2. The electrochemical test sensor of claim 1, wherein the exposed portion of the counter electrode extends across the full width of the capillary space.

3. The electrochemical test sensor of claim 1, wherein the reagent layer includes glucose dehydrogenase.

4. The electrochemical test sensor of claim 1, wherein the exposed portion of the counter electrode is generally T-shaped.

5. The electrochemical test sensor of claim 1, wherein the volume of the capillary space is less than about 1 μL.

6. The electrochemical test sensor of claim 1, further including a spacer, the spacer being located between the lid and the reagent layer.

7. The electrochemical test sensor of claim 1, wherein the lid forms a concave space over the base to assist in forming the capillary space.

8. The electrochemical test sensor of claim 1, wherein the dielectric window includes at least a first section and a second section, the first section having a first width that is different than a second width of the second section.

9. The electrochemical test sensor of claim 8, wherein the dielectric window further includes a third section having a third width that is different than the first width of the first section and the second width of the second section.

10. The electrochemical test sensor of claim 8, wherein the exposed portion of the working electrode is defined in the width-wise dimension by the second width.

11. The electrochemical test sensor of claim 10, wherein the second section of the dielectric window is located on at least a portion of the counter electrode.

12. The electrochemical test sensor of claim 1, wherein the exposed portion of the counter electrode is defined at least in part by an end of the capillary space opposite of the opening.

13. The electrochemical test sensor of claim 1, wherein at least a portion of the width of the exposed portion of the counter electrode is greater than the width of the exposed portion of the working electrode.

14. A method for determining the concentration of an analyte in a fluid test sample with a test sensor, the method comprising the acts of:

providing an electrochemical test sensor including a base, a dielectric layer, a reagent layer and a lid, the base providing a flow path for the fluid test sample having on its surface a counter electrode and a working electrode adapted to electrically communicate with a detector of electrical current, the dielectric layer forming a dielectric window therethrough, the reagent layer including an enzyme that is adapted to react with the analyte, the lid being adapted to mate with the base and to assist in forming a capillary space with an opening for the introduction of the fluid test sample thereto, the dielectric layer and the reagent layer being located between the base and the lid, an exposed portion of the working electrode for being exposed to the fluid test sample being defined in a width-wise dimension by the dielectric window, an exposed portion of the counter electrode for being exposed to the fluid test sample being defined in a width-wise dimension by at least a portion of the dielectric window and at least a portion of the capillary space, the at least a portion of the dielectric window being different from the at least a portion of the capillary space, and a width of the exposed portion of the counter electrode defined by the dielectric window being different than a width of the exposed portion of the counter electrode defined by the capillary space;

contacting the reagent layer with the fluid sample via the capillary space;

generating an electrical signal in the test sensor in response to the presence of the analyte; and determining a level of the analyte from the electrical signal.

* * * * *